US00PP24296P3

(12) United States Plant Patent
Meilland

(10) Patent No.: US PP24,296 P3
(45) Date of Patent: Mar. 11, 2014

(54) GRANDIFLORA ROSE PLANT NAMED 'MEIDYSOUK'

(50) Latin Name: *Rosa hybrida*
Varietal Denomination: Meidysouk

(75) Inventor: Alain A. Meilland, Antibes (FR)

(73) Assignee: CP Delaware, Inc., Wilmington, DE (US)

( * ) Notice: Subject to any disclaimer, the term of this patent is extended or adjusted under 35 U.S.C. 154(b) by 52 days.

(21) Appl. No.: 13/507,651

(22) Filed: Jul. 17, 2012

(65) Prior Publication Data

US 2014/0026264 P1 Jan. 23, 2014

(51) Int. Cl.
*A01H 5/00* (2006.01)

(52) U.S. Cl.
USPC ..... Plt./130

(58) Field of Classification Search
USPC ..... Plt./130
See application file for complete search history.

*Primary Examiner* — Annette Para
(74) *Attorney, Agent, or Firm* — Buchanan Ingersoll & Rooney PC

(57) ABSTRACT

A new and distinct variety of Grandiflora rose plant is provided that abundantly and substantially continuously forms attractive very double strongly fragrant light orange suffused with light red blossoms that well drop petals upon full maturity. The vegetation is strong. A vigorous bushy growth habit is displayed. The disease resistance is very good, particularly with respect to *Botrytis*. The plant is well suited for providing distinctive attractive ornamentation in the landscape.

1 Drawing Sheet

Botanical/commercial classification: *Rosa hybrida*/Grandiflora Rose Plant.

Varietal denomination: cv. Meidysouk.

SUMMARY OF THE INVENTION

The new variety of *Rosa hybrida* Grandiflora rose plant was created in France by artificial pollination wherein two parents were crossed which previously had been studied in the hope that they would contribute the desired characteristics. The female parent (i.e., the seed parent) was the 'Meirestif' variety (non-patented in the United States). The male parent (i.e., pollen parent) was the product of the cross of the 'Meicapinal' variety (non-patented in the United States) and the 'Ausmas' variety (non-patented in the United States).

The parentage of the new variety can be summarized as follows:

('Meirestif'×'Meicapinal')×'Ausmas'.

The seeds resulting from the above pollination were sown and small plants were obtained which were physically and biologically different from each other. Selective study resulted in the identification of a single plant of the new variety.

It was found that the new Grandiflora rose plant of the present invention:

(a) forms strong vegetation,
(b) displays a vigorous bushy growth habit with very dense dark green foliage having a glossy upper surface,
(c) abundantly and substantially continuously forms attractive very double strongly fragrant light orange suffused with light red blossoms that well drop petals upon full maturity,
(d) displays very good disease resistance particularly with respect to *Botrytis*, and
(e) is well suited for providing distinctive attractive ornamentation in the landscape.

The light blossom coloration contrasts nicely with the glossy dark green foliage.

The new variety well meets the needs of the horticultural industry and can be grown to advantage in parks and gardens.

The new variety can be readily distinguished from its ancestors upon an inspection of the blossoms. More specifically, the 'Meirestif' variety forms ocher colored blossoms, the 'Meicapinal' variety forms medium pink colored blossoms, and the 'Ausmas' variety forms rich deep yellow colored blossoms.

The new variety has been found to undergo asexual propagation at Le Cannet des Maures, Var, France, by a number of routes, including budding, grafting, and the use of cuttings. Such asexual propagation by the abovementioned techniques has shown that the characteristics of the new variety are stable and are strictly transmissible by such asexual propagation from one generation to another. Accordingly, the new variety undergoes asexual propagation in a true-to-type manner.

The new variety has been named 'Meidysouk'.

BRIEF DESCRIPTION OF THE PHOTOGRAPH

The accompanying photograph shows as nearly true as it is reasonably possible to make the same in a color illustration of this character, typical specimens of plant parts of the new variety. The rose plants of the new variety were approximately two years of age and were observed during May while asexually reproduced from cuttings and growing outdoors on their own roots at Le Cannet des Maures, Var, France. Standard color information is provided at the bottom of the photograph for comparative purposes.

FIG. 15 illustrates a specimen of a leaf with 5 leaflets—plan view—under surface (left) and—upper surface (right).

DETAILED DESCRIPTION

Figures 1, 2, 3, 4, 5, 6, 7, 8, 9, 10, 11, 12, 13, 14:
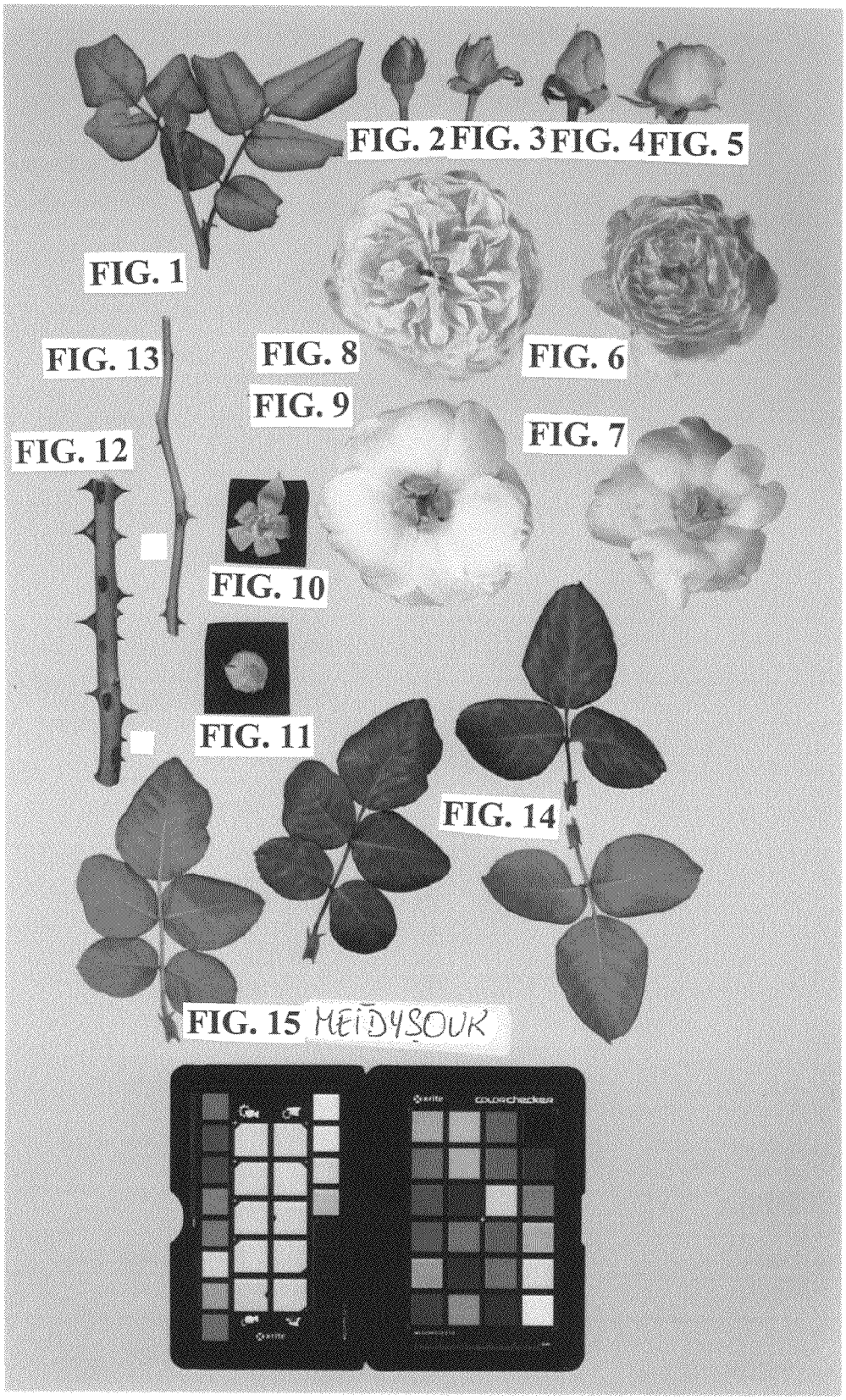
FIG. 1 illustrates a specimen of a young shoot.
FIG. 2 illustrates a specimen of a floral bud before the opening of the sepals.
FIG. 3 illustrates a specimen of a floral bud at the opening of the sepals.
FIG. 4 illustrates a specimen of a floral bud at the opening of the petals.
FIG. 5 illustrates a specimen of a flower in the course of opening.
FIG. 6 illustrates a specimen of an open flower—plan view—obverse.
FIG. 7 illustrates a specimen of an open flower—plan view—reverse.
FIG. 8 illustrates a specimen of a fully open flower—plan view—obverse.
FIG. 9 illustrates a specimen of a fully open flower—plan view—reverse.
FIG. 10 illustrates a specimen of a floral receptacle showing arrangement of the stamens and pistils.
FIG. 11 illustrates a specimen of a floral receptacle showing arrangement of the pistils (stamens removed)
FIG. 12 illustrates a specimen of a main branch.
FIG. 13 illustrates a specimen of a flowering stem.
FIG. 14 illustrates a specimen of a leaf with 3 leaflets—plan view—upper surface (top) and—under surface (bottom)

The chart used in the identification of the colors is that of The Royal Horticultural Society (R.H.S. Colour Chart—1995 or equivalent) except where ordinary color terms are utilized. Such common color terms are to be accorded their customary dictionary significance. The description is based upon the observation of plants of the new variety at an age of approximately two years during the month of May while being grown on their own roots at Le Cannet des Maures, Var, France.

Class: Grandiflora.

Plant:

*Growth habit*.—Bushy.

Branches:

*Color*.—Young stems: commonly near Yellow-Green Group 144A with some anthocyanin coloration of near Greyed-Red Group 178A. adult wood: commonly near Yellow-Green Group 146B.

*Thorns*.—Configuration: curved downwards on the upper surface and slightly concave on the under surface with an oval base. quantity and size on young stems: commonly approximately 13 on average having lengths of approximately 6 to 9 mm over a stem length of 10 cm, and commonly bear no small prickles. quantity and size on adult stems: commonly approximately 16 on average having lengths of approximately 6 to 9 mm over a stem length of 10 cm, and commonly bear no small prickles. color on young stems: near Greyed-Red Group 181A. color on adult stems: near Greyed-Red Group 181C.

Leaves:

*Overall appearance*.—Very dense dark green.

*Leaflets*.—Shape: generally oval. number 3, and most often 5 and 7. apex: cuspidate. base: rounded. size: the terminal leaflets commonly are approximately 5.4 cm in length on average and approximately 4.5 cm in width on average. serration: slightly denticulate, small and single. texture: firm, and smooth, and glossy on the upper surface. color (young foliage): near Green Group 137B on the upper surface, and near Green Group 138B on the under surface. color (adult foliage): near Green Group 137A on the upper surface, and near Green Group 138B on the under surface.

*Petiole*.—Length: commonly approximately 3 to 3.5 cm on average. texture: slightly glandular on the upper surface and commonly with a few prickles on the under surface. color: with anthocyanin coloration of Greyed-Orange Group 175A on the upper surface, and near Yellow-Green Group 148C on the under surface.

*Rachis*.—Color: near Yellow-Green Group 145B and 145C on the upper surface, and near Yellow-Green Group 146C on the under surface.

*Stipules*.—General appearance: adnate, pectinate, and relatively broad. size: commonly approximately 1.2 to 2 cm in length on average, and approximately 7 to 9 mm in width on average. color: near Yellow-Green Group 145B and 145C on the upper surface, and near Yellow-Green Group 146C on the under surface.

Inflorescence:

*Number of flowers*.—Commonly approximately 1 to 5 fully double blossoms per stem.

*Peduncle*.—Glandular, commonly approximately 4.2 cm in length on average, approximately 5 mm in diameter on average, and near Yellow-Green Group 146C in coloration.

*Sepals*.—Shape: longish and narrowly pointed, and somewhat rounded at the base. texture: tomentose on upper surface, and smooth on the under surface. size: approximately 3.2 cm in length on average, and approximately 1.6 cm in width on average at the base. color: near Yellow-Green Group 148C on the upper surface, and near Yellow-Green Group 148B on the under surface.

*Buds*.—Shape: generally ovate and large. length: approximately 2.5 cm on average. width: approximately 2.3 cm at the widest point on average. color: as the calyx breaks, near Yellow-Orange Group 16B and 16C on the upper surface, and Yellow-Orange Group 16B margined with near Red Group 47C on the under surface.

*Flower*.—Diameter: approximately 11 to 14 cm on average. shape: cup-shaped. color (in course of opening): upper side: near Yellow Group 4D, amply suffused with near Red Group 36C and 36D, margined with near Red Group 51D, and with a spot at the base of near Yellow Group 12B. under side: near Orange Group 27B, 27C, and 27D, and suffused and margined with Red Group 54D. color (when open): upper side: near Orange Group 27D, suffused and margined with near Red Group 56D, and with a spot of near Yellow Group 12B at the base. under side: nearly Orange Group 27D, and suffused and margined with near Red Group 56D. fragrance: strong. petal number: commonly approximately 66 to 71 on average under normal growing conditions. petal shape: commonly display a rounded tip and an obtuse base. petal arrangement: imbricated and commonly without petaloids. petal texture: firm. petal length: commonly approximately 5.5 cm on average. petal width: commonly approximately 5.5 cm on average. petal drop: good with the petals commonly detaching cleanly before drying. stamen number: commonly approximately 94 on average. anthers: arranged regularly around the styles, commonly approximately 0.2 cm in size on average, and near Yellow-Orange Group 14D in coloration. filaments: commonly approximately 7 to 9 mm in length on average, and near Greyed-Red Group 181C in coloration. pistils: commonly approximately 72 on average. styles: commonly approximately 1 mm in size on average, and near Orange Group 27D in coloration. stigmas: commonly approximately 4 mm in size and near Greyed-Red Group 181D in coloration. receptacle: pitcher-shaped, commonly approximately 1.2 cm in length on average, commonly approximately 1.1 cm in width at the widest point, smooth in texture, and near Yellow-Green Group 146C in coloration.

Development:

*Vegetation*.—Very strong.

*Blooming*.—Medium season, abundant and substantially continuous.

*Tolerance to diseases*.—Very good, particularly with respect to *Botrytis*.

I claim:

1. A new and distinct Grandiflora rose plant characterized by the following characteristics:

(a) forms strong vegetation, (b) displays a vigorous bushy growth habit with very dense dark green foliage having a glossy upper surface, (c) abundantly and substantially continuously forms attractive very double strongly fragrant light orange suffused with light red blossoms that well drop petals upon full maturity, (d) displays very good disease resistance particularly with respect to *Botrytis*, and (e) is well suited for providing distinctive attractive ornamentation in the landscape;

substantially as shown and described.

* * * * *

FIG. 15 MEIDYSOUK
COLORCHECKER